(12) United States Patent
Schultz

(10) Patent No.: US 10,966,783 B2
(45) Date of Patent: Apr. 6, 2021

(54) CATHETER WITH MULTIFUNCTIONAL MICROINJECTION—MOLDED HOUSING

(71) Applicant: BIOSENSE WEBSTER (ISRAEL) LTD., Yokneam (IL)

(72) Inventor: Jeffrey William Schultz, Chino, CA (US)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 379 days.

(21) Appl. No.: 15/925,521

(22) Filed: Mar. 19, 2018

(65) Prior Publication Data

US 2019/0282297 A1 Sep. 19, 2019

(51) Int. Cl.
| | |
|---|---|
| *A61B 18/14* | (2006.01) |
| *A61B 5/00* | (2006.01) |
| *A61B 17/00* | (2006.01) |
| *A61B 18/00* | (2006.01) |
| *A61M 25/00* | (2006.01) |

(Continued)

(52) U.S. Cl.
CPC ........ *A61B 18/1492* (2013.01); *A61B 5/6852* (2013.01); *A61M 25/0043* (2013.01); *A61M 25/0068* (2013.01); *A61B 2017/00318* (2013.01); *A61B 2018/00029* (2013.01); *A61B 2018/00351* (2013.01); *A61B 2018/00577* (2013.01); *A61B 2090/064* (2016.02);
(Continued)

(58) Field of Classification Search
CPC .............. A61B 18/1492; A61B 5/6852; A61B 2018/0577; A61B 2218/002; A61B 2090/064; A61B 2090/065; A61B 2017/00318; A61B 18/14; A61B 18/12; A61B 5/065; A61B 5/6843; A61B 2562/0261; A61M 25/0043; A61M 25/0068
See application file for complete search history.

(56) References Cited

U.S. PATENT DOCUMENTS

| | | | |
|---|---|---|---|
| 5,454,787 A | * | 10/1995 | Lundquist .......... A61B 10/0233 604/95.01 |
| 7,377,906 B2 | | 5/2008 | Selkee |

(Continued)

OTHER PUBLICATIONS

EPO Extended European Search Report dated Jul. 11, 2019 for EP Application No. 19163470.8, 7 pages.

*Primary Examiner* — Daniel W Fowler
*Assistant Examiner* — Caitlyn E May
(74) *Attorney, Agent, or Firm* — Lewis Roca Rothgerber Christie LLP

(57) ABSTRACT

An electrophysiology catheter has a distal electrode section having a generally-cylindrical, hollow housing body, a lumen and an opening in a sidewall. A flex circuit has a first portion supported on the outer surface the housing body, and a second portion that extends into the lumen via the opening for connection to cables and/or wires in the lumen. The flex circuit has a first and second magnetic field sensing coil traces generally perpendicular to each other and a magnetic field sensing coil wire generally perpendicular thereto is wound around the housing body to form an x/y/z position sensor. One or more ring electrodes are carried on the housing body, separated by ring spacers. A force sensor is mounted on a distal end of the housing body, with strain gauges electrically connected to the flex circuit. The housing is configured to provide a distal anchor for a puller tensile.

19 Claims, 6 Drawing Sheets

(51) Int. Cl.
  *A61B 90/00* (2016.01)
  *A61M 25/01* (2006.01)
(52) U.S. Cl.
  CPC ... *A61B 2090/065* (2016.02); *A61B 2218/002* (2013.01); *A61M 25/0136* (2013.01)

(56) References Cited

U.S. PATENT DOCUMENTS

| | | | |
|---|---|---|---|
| 8,357,152 B2 | 1/2013 | Govari et al. | |
| 8,792,962 B2 | 7/2014 | Esguerra et al. | |
| 9,037,213 B2 * | 5/2015 | Roth | G01R 33/028 600/410 |
| 9,101,734 B2 | 8/2015 | Selkee | |
| 2003/0187347 A1 * | 10/2003 | Nevo | A61B 5/06 600/424 |
| 2007/0219551 A1 * | 9/2007 | Honour | A61B 18/1492 606/41 |
| 2008/0255540 A1 | 10/2008 | Selkee | |
| 2009/0171187 A1 * | 7/2009 | Gerhart | A61B 5/042 600/421 |
| 2010/0168827 A1 | 7/2010 | Schultz | |
| 2011/0130648 A1 | 6/2011 | Beeckler et al. | |
| 2012/0197109 A1 * | 8/2012 | Hartmann | A61B 34/20 600/424 |
| 2014/0018788 A1 * | 1/2014 | Engelman | A61B 18/18 606/33 |
| 2014/0163548 A1 * | 6/2014 | Christian | A61B 18/1492 606/41 |
| 2015/0011843 A1 * | 1/2015 | Toth | A61N 1/36185 600/301 |
| 2015/0073514 A1 * | 3/2015 | Ku | A61M 25/0074 607/96 |
| 2016/0143690 A1 | 5/2016 | Schultz et al. | |
| 2017/0035989 A1 * | 2/2017 | Gilman | A61M 25/001 |

* cited by examiner

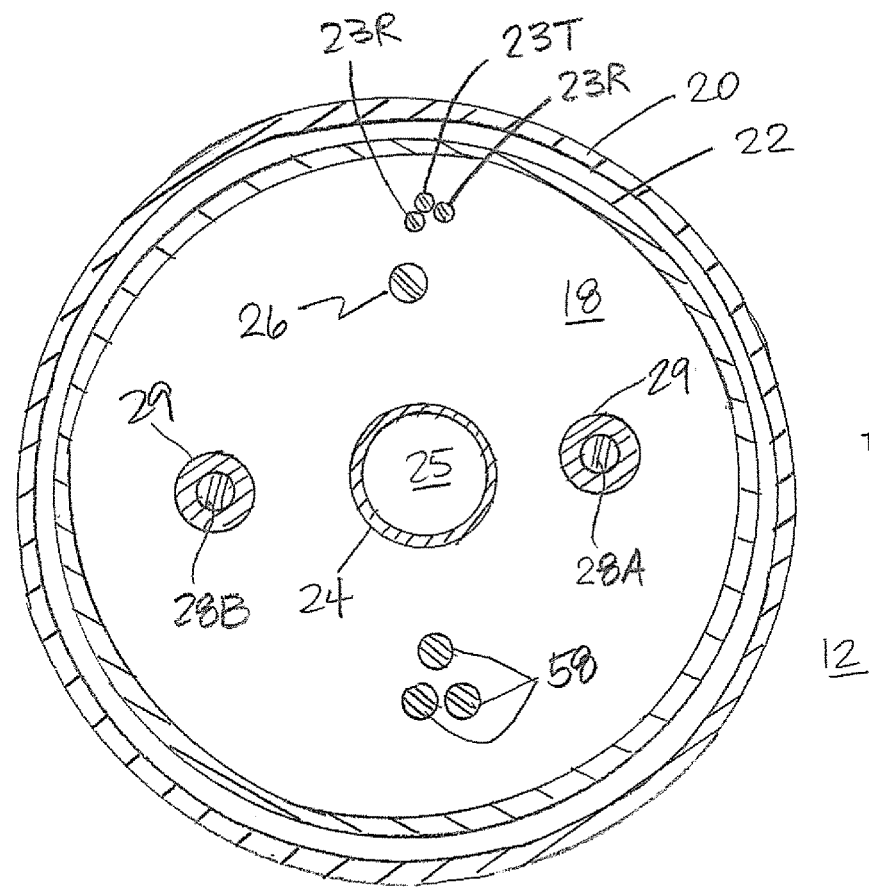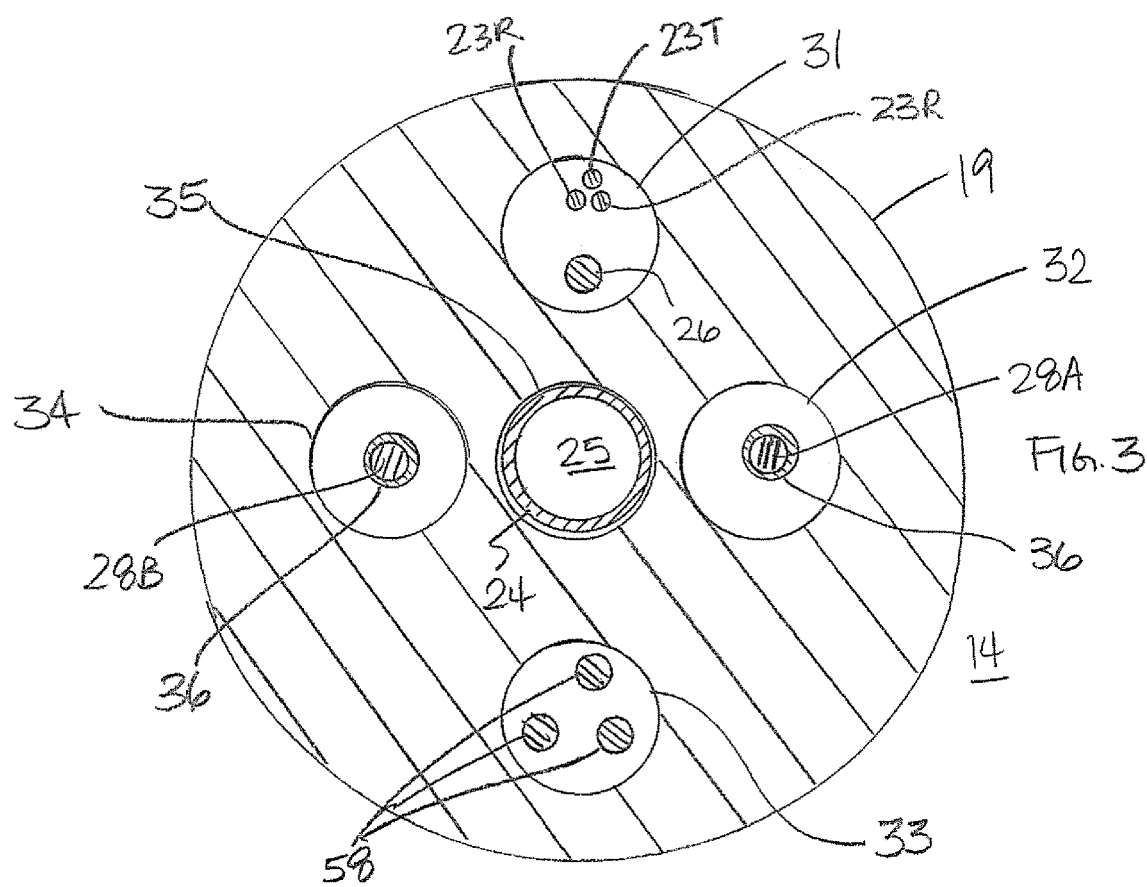

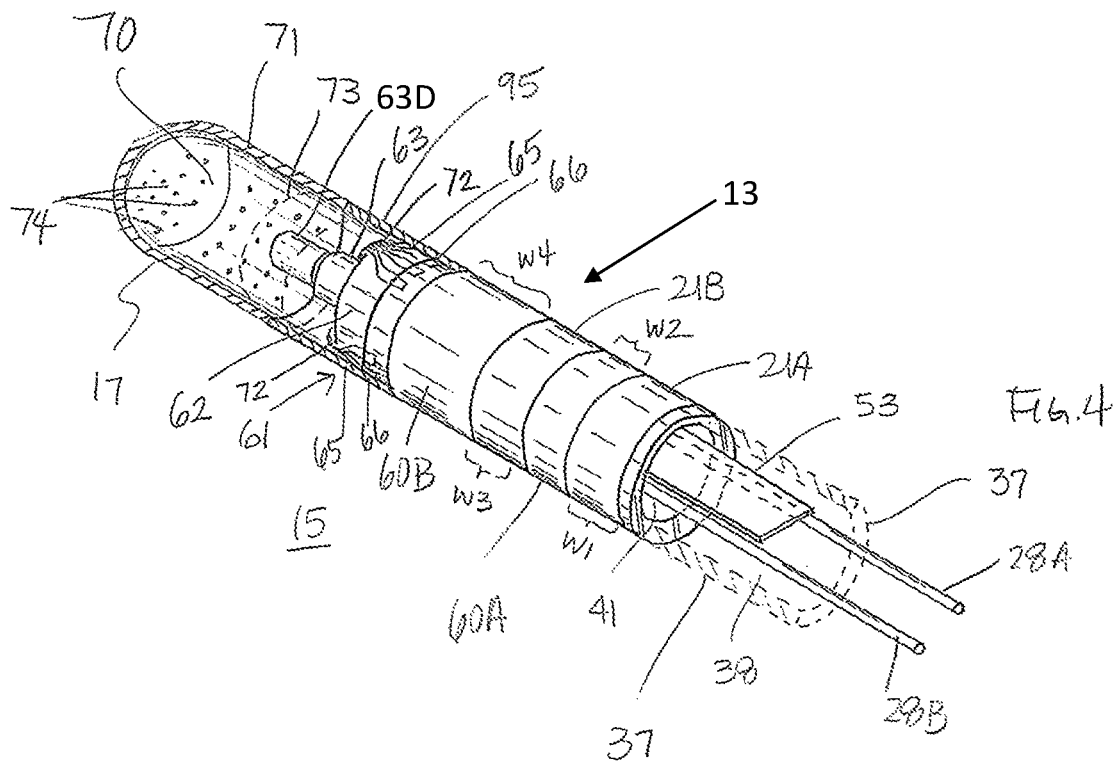
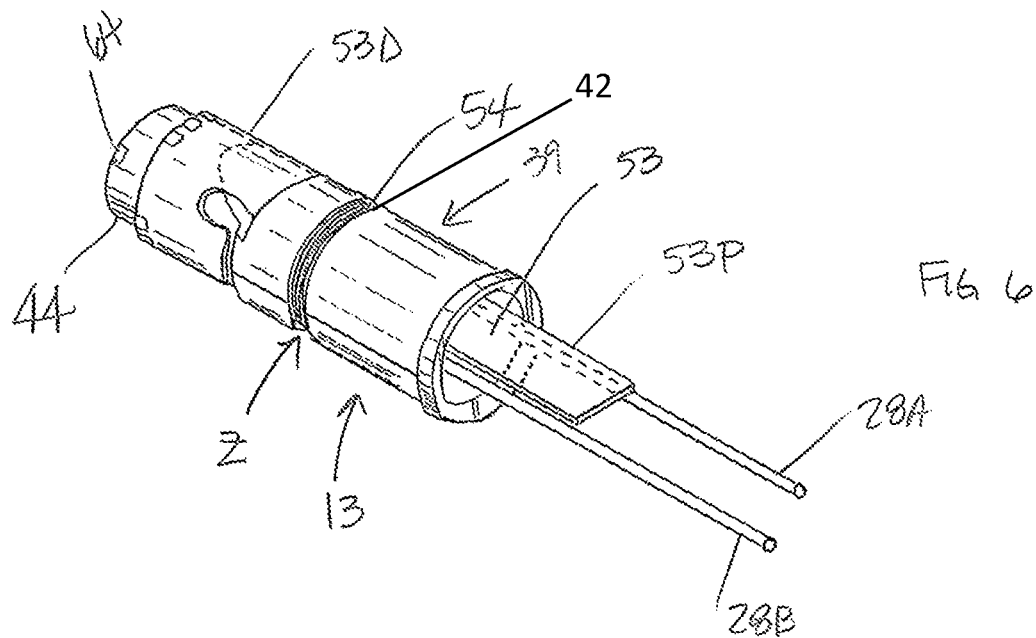

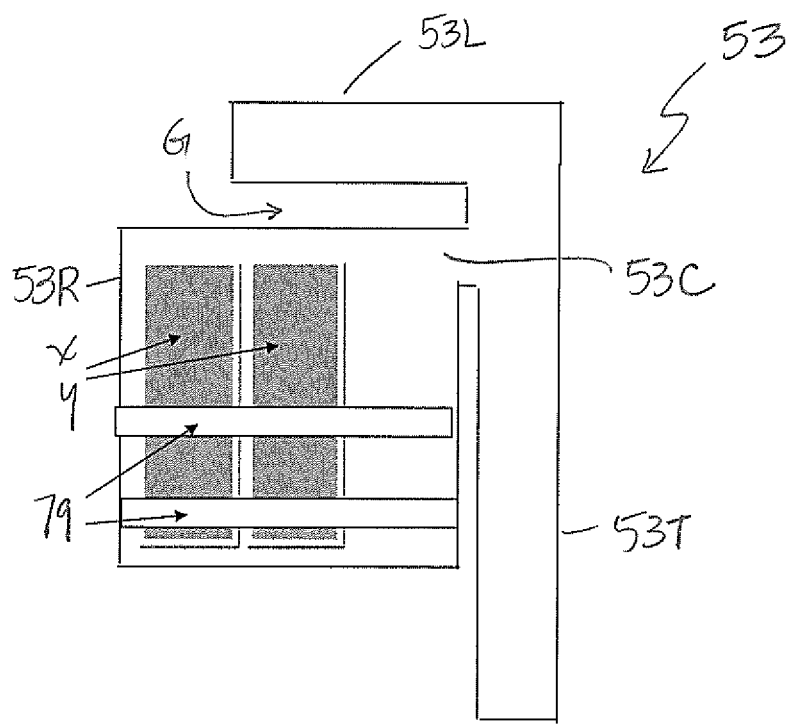

CATHETER WITH MULTIFUNCTIONAL MICROINJECTION—MOLDED HOUSING

FIELD OF INVENTION

The present invention relates to electrophysiologic (EP) catheters, in particular, EP catheters for ablating cardiac tissue.

BACKGROUND

Electrode catheters have been in common use in medical practice for many years. Diagnosis and treatment of cardiac arrythmias by means of electrode catheters include mapping the electrical properties of heart tissue and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall.

In a two-step procedure-mapping followed by ablation-electrical activity at locations within the heart is typically sensed and measured by advancing a catheter containing one or more electrical sensors (or electrodes) into the heart, and acquiring data at a multiplicity of locations. These data are then utilized to select the tissue target areas at which ablation is to be performed.

In use, the electrode catheter is inserted into a major vein or artery, e.g., the femoral artery, and then guided into the chamber of the heart which is of concern. A reference electrode is provided, generally taped to the patient's skin or provided on the ablation catheter or another catheter. Radio frequency (RF) current is applied to the ablation electrode of the catheter, and flows through the surrounding media, i.e., blood and tissue, toward the reference electrode. The distribution of current depends on the amount of electrode surface in contact with the tissue, as compared to blood which has a higher conductivity than the tissue.

The distal electrode section of conventional irrigated catheters is a location of multiple functions and purposes. The location may include anchors for distal ends of puller wires or tensile members. The location may also house an electromagnetic position sensor. A force sensor may also be included in that location. One or more ring electrodes may also be present at that location. Consequently, the distal electrode section is often cramped with components crisscrossing and overlapping each other, making assembly a challenge and the distal electrode section an area where damage and defects can occur.

Accordingly, there is a desire for a catheter whose distal electrode section has a more simplified structure and arrangement, with improved integration of multiple different components. There is also a desire to use flex circuits for integration of electrical conductors because flex circuits are more adaptable and reduce clutter and can be electrically connected with the use of electrical traces.

SUMMARY OF THE INVENTION

An electrophysiology catheter has a distal electrode section having a micro injection molded housing component with multiple features to facilitate multiple functions, including puller tensile member anchor, integration of electromagnetic position sensor, connection to force sensor, ring electrode placement and simplified integration of electrical conductors and contacts. The distal electrode section has a more simplified structure and arrangement. Moreover, the distal electrode section includes flex circuits for integration of electrical conductors because flex circuits are more adaptable to space constraints and can eliminate the use of traditional welding process for connecting ring electrodes. Furthermore, flex circuits may be more easily integrated into the distal electrode section with the use of electrical traces which can be applied by deposition methods.

In some embodiments, an electrophysiology catheter has an elongated catheter body, a deflection section distal of the catheter body, a distal electrode section and a control handle proximal of the catheter body. The distal electrode section includes a housing with a generally-cylindrical, hollow housing body with an outer surface, a lumen and an opening in a sidewall allowing access into the lumen. The distal electrode section also includes a flex circuit having a first portion supported on the outer surface of the housing body and a second portion extending into the lumen via the opening in the housing body.

In some embodiments, the housing body has a microinjection molded construction.

In some embodiments, the flex circuit has a first magnetic field sensing coil trace, and a second magnetic field sensing coil trace generally perpendicular to the first magnetic field sensing coil.

In some embodiments, the first and second magnetic field sensing coil traces are electrically connected to one or more cables extending through the catheter body and the deflection section.

In some embodiments, the distal electrode section includes a magnetic field sensing coil wire wound around the housing body, wherein the third magnetic field sensing coil wire is generally perpendicular to the first and second magnetic field sensing coil traces.

In some embodiments, the outer surface of the housing body has a circumferential recess and the third magnetic field sensing coil wire is situated in the circumferential recess.

In some embodiments, the distal electrode assembly includes a ring electrode and a ring spacer on the outer surface of the housing body.

In some embodiments, the housing body has a ridge at its proximal end, and the ring electrode distal of the ridge abuts the ridge, and the ring spacer distal of the ring electrode abuts the ring electrode.

In some embodiments, the housing body has a ridge at its proximal end, and the ring spacer distal of the ridge abuts the ridge, and the ring electrode distal of the ring space abuts the ring spacer.

In some embodiments, the distal electrode section further comprises a force sensor mounted on a distal end of the housing body.

In some embodiment, the force sensor has a plurality of strain gauges electrically connected to the flex circuit.

In some embodiments, the force sensor has an on-axis stem and an annular ring generally perpendicular to the stem, wherein the strain gauges extend between the stem and the annular ring.

In some embodiment, the distal electrode section includes a tip electrode distal of the housing body, wherein the tip electrode has a shell portion, a plug portion and an internal chamber configured to receive fluid.

In some embodiments, the catheter includes a fluid tubing extending through the catheter body and the deflection and further into the distal electrode section, wherein the fluid tubing has a distal end configured to pass fluid into the internal chamber of the tip electrode.

In some embodiment, the catheter includes a puller tensile member having a U-bend portion anchored in the housing body.

In some embodiments, the housing body has a through-opening through which the puller tensile member extends.

In some embodiments, the housing body has two through-openings, each through which a respective portion of the puller tensile member extends.

In some embodiments, the housing body has a recess in which the U-bend portion of the puller tensile member lies.

In some embodiments, the recess is arcuate around a distal opening of the lumen of the housing body.

In some embodiments, the housing body has a step between a distal portion with a smaller outer diameter and a proximal portion with a larger diameter, wherein the first portion of the flex circuit is supported on the distal portion of the housing body.

In some embodiments, the magnetic sensing coil wire is wound on the proximal portion of the house body.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 2 is an end cross-sectional view of a catheter body of the catheter of FIG. 1, taken along line A-A.

FIG. 3 is an end cross-sectional view of an intermediate deflection section of the catheter of FIG. 1, taken along line B-B.

FIG. 4 is a perspective view of a distal section of the catheter, with parts broken away, in accordance with an embodiment.

FIG. 6 is a perspective view of the housing of FIG. 5A, with a force sensor, in accordance with an embodiment.

FIG. 9 is a top view of a flex circuit lying flat, in accordance with another embodiment.

DETAILED DESCRIPTION OF THE INVENTION

Figure 1:
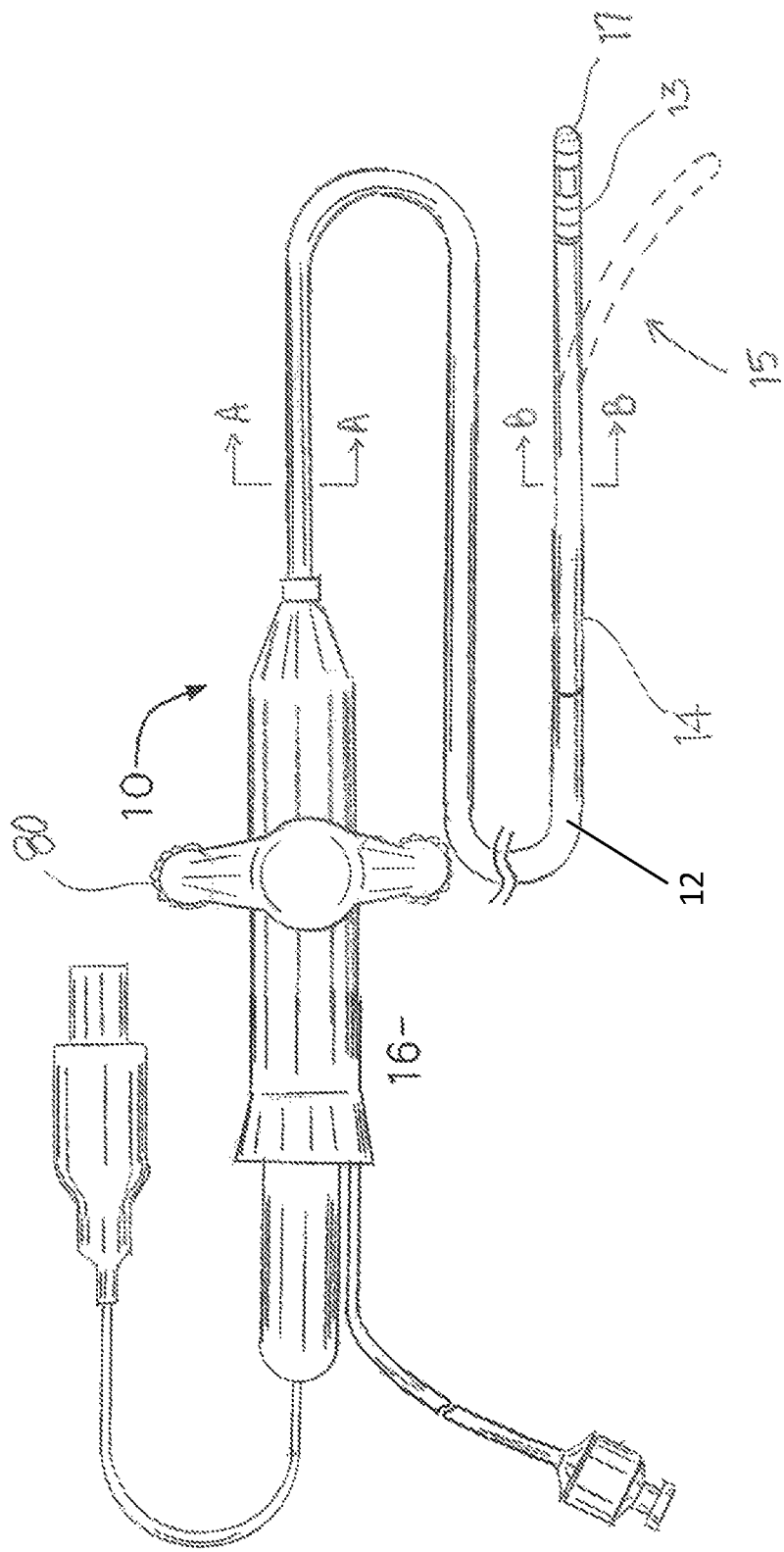
FIG. 1 is a perspective view of a catheter of the present invention, in accordance with an embodiment.

FIG. 1 illustrates an embodiment of a catheter 10 having an elongated catheter body 12 with proximal and distal ends, an intermediate deflectable section 14 at the distal end of the catheter body 12, and a distal electrode section 15 with a tip electrode 17 and a micro-injection molded, multi-functional housing 13. The catheter also includes a control handle 16 at the proximal end of the catheter body 12 for controlling bi-directional deflection of the intermediate section 14 relative to the catheter body 12.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. In some embodiments, the catheter body 12 comprises an outer wall 20 made of polyurethane or PEBAX with an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical. In some embodiments, the outer diameter is about 8 french or 7 french. Likewise the thickness of the outer wall 20 is not critical, but is thin enough so that the central lumen 18 can accommodate components, e.g., puller tensile members, lead wires, and any other desired wires, cables or tubings. If desired, the inner surface of the outer wall 20 is lined with a stiffening tube 22 to provide improved torsional stability. In some embodiments, the catheter has an outer wall 20 with an outer diameter of from about 0.090 inch to about 0.94 inch and an inner diameter of from about 0.061 inch to about 0.065 inch.

The components extending through the lumen 18 of the catheter body 12 may include lead wires 23T and 23R (for the tip electrode 17 and one or more ring electrodes 21 proximal of the tip electrode), an irrigation tubing 24 with lumen 25 for delivering fluid to the tip electrode, one or more wire(s) and/or cable(s) (collectively "cables") 26 for an EM position sensor 27 carried in or near the distal section 15, one wire(s) and/or more cable(s) (collectively "cables") 58 for a force sensor 61 housed in the distal section 15, and/or puller tensile members 28A, 28B for deflecting the intermediate section 14.

FIG. 3 illustrates an embodiment of the intermediate section 14 which comprises a short section of tubing 19. The illustrated tubing 19 has multiple lumens, for example off-axis lumens 31, 32, 33, 34 and on-axis lumen 35. In some embodiments, the lumen 31 carries the lead wires 23T and 23R, and the position sensor cables 26, the lumen 32 carries the first puller tensile member 28A, the lumen 33 carries the force sensor cables 58, the lumen 34 carries the second puller tensile member 28B, and the lumen 35 carries the irrigation tubing 24. It is understood that the lumens may be arranged in different configurations, as needed or appropriate.

The tubing 19 of the intermediate section 14 is made of a suitable non-toxic material that is more flexible than the catheter body 12. A suitable material for the tubing 19 is braided polyurethane, i.e., polyurethane with an embedded mesh of braided stainless steel or the like. The size of each lumen is not critical, but is sufficient to house the respective components extending therethrough.

Each puller tensile member 28A, 28B has a lubricious coating, e.g. of Teflon®. The puller tensile members can be made of any suitable metal, such as stainless steel, Nitinol or Vectran® and the Teflon coating imparts lubricity to the puller tensile member. In some embodiments, the puller tensile member has a diameter ranging from about 0.006 to about 0.010 inch.

As shown in FIG. 2, the portion of each puller tensile member 28A, 28B in the catheter body 12 passes through a respective compression coil 29 in surrounding relation. Each compression coil extends from the proximal end of the catheter body 12 to at or near the proximal end of the intermediate section 14. The compression coils are made of any suitable metal, preferably stainless steel, and are tightly wound on themselves to provide flexibility, i.e., bending, but to resist compression. The inner diameter of the compression coil is slightly larger than the diameter of the puller tensile member. As shown in FIG. 3, each portion of the puller tensile members 28A, 28B distal of the compression coil may extend through a respective protective sheath 36 to prevent the puller tensile member from cutting into the tubing 19 of the intermediate section 14 during deflection.

Proximal ends of the puller tensile members 28A, 28B are anchored in the control handle 16 to deflection actuation mechanisms that are responsive to an operator's manipulation of a deflection knob 80 of the control handle 16. Suitable deflection members are described in U.S. Pat. No. 7,377,906, titled STEERING MECHANISM FOR BI-DIRECTIONAL CATHETER, the entire disclosure of which is incorporated herein by reference.

With reference to FIG. 4, at the distal end of the intermediate section 14 is the distal electrode section 15 that includes the tip electrode 17, the micro-injection molded, multifunctional housing 13, and a flex circuit 53 supported by the housing 13. In some embodiments, a relatively short piece of non-conductive, single-lumened connector tubing 37 extends between the housing 13 and the distal end of the tubing 19, to provide a lumen 38 which allows components passing between the lumen 41 of the housing 13 and the lumens 31-35 of the tubing 19 (see FIG. 3) to reorient, as needed. These components may include, for example, the electrode lead wires 23T, 23R, the irrigation tubing 24, the force sensor cables 58, the puller tensile members 28A, 28B, and the EM position sensor cables 58 (see FIG. 3).

Figure 5A:
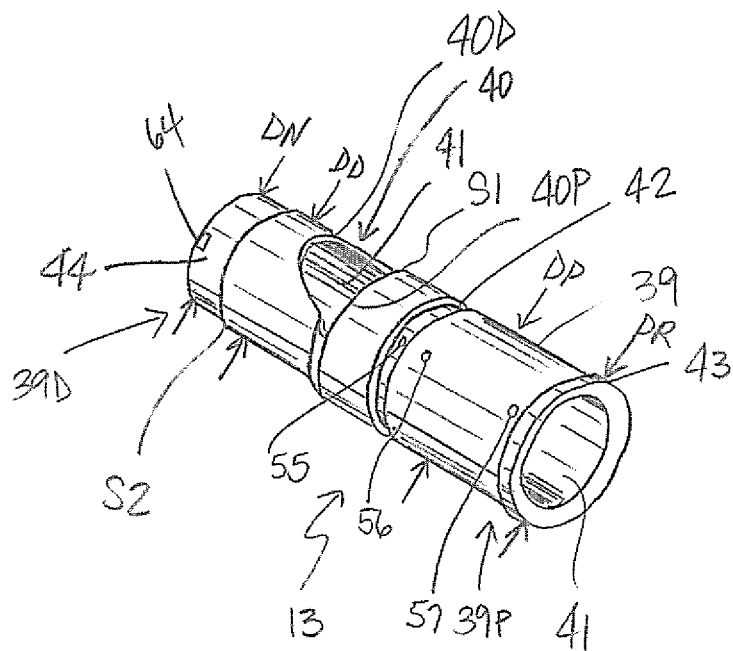
FIG. 5A is a perspective view of a multifunctional micro-injection-molded housing of the distal section of FIG. 4.
Figure 5B:
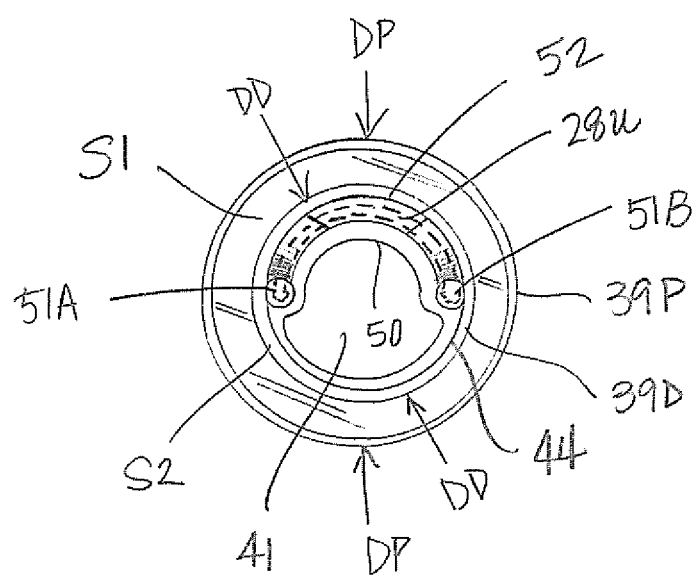
FIG. 5B is an end cross-sectional view of the housing of FIG. 5A, taken along line A-A.

As shown in FIG. 5A and FIG. 5B, the micro-injection molded, multifunctional housing 13 has a generally hollow cylindrical body 39 having a lumen 41, a distal portion 39D with an outer diameter DD and a proximal portion 39P with an outer diameter DP, with DD<DP creating a first circumferential step S1 at the junction between the portions 39D and 39P. The body 39 also has a radial opening 40 in a sidewall of the distal portion 39D that provides access into the lumen 41. The opening 40 has a proximal edge 40P that lies along the step S1 and a distal edge 40D that has an arcuate configuration. The outer surface of the distal portion 39D is generally smooth. The outer surface of the proximal portion 39P is generally smooth with the exception of a circumferential recess 42 extending around the body 39.

At the proximal end, the body 39 has an annular ridge 43 whose outer diameter DR>DP. The body 39 has a short distal end portion or neck 44 whose outer diameter DN<DD creates a second or distal circumferential step S2.

The lumen 41 extends through the entirety of the body 39. The lumen 41 at least at the distal end of the body 39 is partially occluded by a partial peripheral lip 50 that projects inwardly into the lumen 41 (FIG. 5B). The lip 50 includes two axial through-holes 51A, 51B generally aligned with lumens 32 and 34, respectively, of the multi-lumened tubing 19 of the deflection section 14. Connecting the through-holes 51A, 51B is a curved elongated recess 52 on a distal face of the lip 50 that follows the peripheral curvature of the lip 50. In that regard, it is understood that the puller tensile members 28A and 28B may be portions of a single puller tensile member that has a U-bend portion 28U (shown in broken lines) that nests in the elongated recess 52 with each leg extending through a respective through-hole 51A, 51B as portions 28A, 28B, respectively. The curved elongated recess 52 anchors the U-bend portion 28U so that an operator manipulating a deflection knob 80 of the control handle 16 (FIG. 1) acting on proximal ends of the portions 28A, 28B can deflect the deflection section 14 bi-directionally. The curved elongated recess 52 anchors the U-bend portion 28U in a manner that minimizes occlusion or occupation of the lumen 41.

The lip 50 may be a formation limited to the distal end of the body 39. In some embodiments, the lip 50 may be a formation that extends along the inner surface surrounding the lumen, as appropriate or desired. In this regard, the through-holes 51A/51B are elongated passages that extend the length of the body 39.

Figure 7:
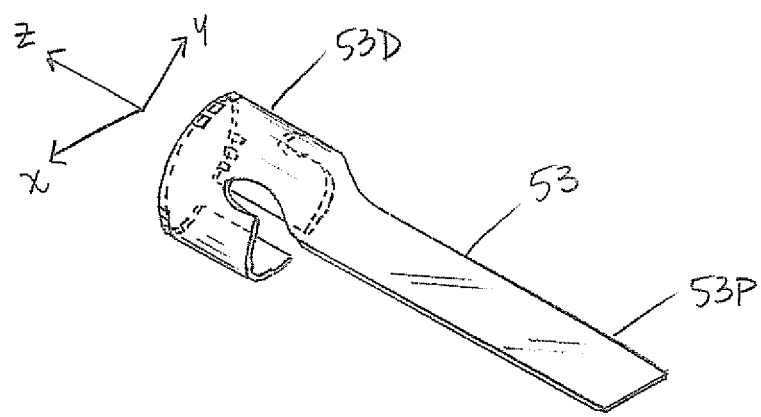
FIG. 7 is a perspective view of a flex circuit of FIG. 6.
Figure 8:
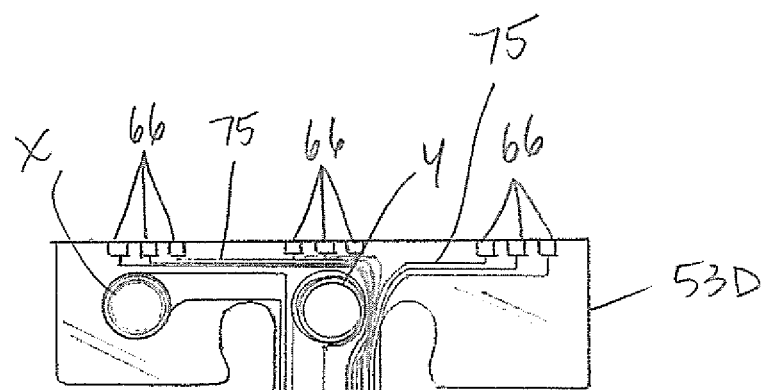
FIG. 8 is a top view of the flex circuit of FIG. 7 lying flat.

As shown in FIG. 6, a flex circuit 53 is supported by the housing 13. In some embodiments, the flex circuit has a T-configuration, with a generally rectangular distal portion 53D and an elongated proximal portion or tail 53P extending at about 90 degrees, as shown in FIG. 7 and FIG. 8. The distal portion 53D has traces X configured as an x-axis coil and traces Y configured as a y-axis coil. The distal portion 53D is wrapped around the outer surface of the distal portion 39D such that the coil traces X and Y are generally perpendicular to each other on outer surface of the distal portion 39D.

The proximal portion or tail 53P advantageously extends into the lumen 41 via the opening 40 in the body 39. The proximal portion 53P includes traces Tx, Ty and connection pads 76 that connect to one or more electrical components, including the EM position sensor cables 26 for passing electrical signals arising in the coil traces X and Y proximally along the deflection section 14 and the catheter body 12, toward the control handle 16. A z-axis coil Z includes a wire 54 wrapped around the circumferential recess 42 of the body 39 (see FIG. 6). End portions of the wire 54 extend through one or more through-hole 55 (see FIG. 5A) formed in the sidewall of the recess 42 to reach the lumen 41 of the housing body 39, where the end portions are joined with the flex circuit 53 or EM sensor cable 26.

In some embodiments, the end portions of the wire 54 are soldered directly to connection pads on the flex circuit 53 without routing them through the lumen 41 of the body 39. In some embodiments, with reference to FIG. 5A and FIG. 9, a flex circuit 53 has a distal portion or leg 53L and a longitudinal proximal portion or tail 53T which together form an "L" shape. On the same side as the distal leg 53L and proximal thereof by a separation gap G, the flex circuit 53 includes a generally rectangular proximal portion 53R with a corner 53C that extends from a side edge of the tail 53T. The distal leg 53L is configured to wrap circumferentially around the distal portion 39D of the body 39, the tail 53T is configured to pass through the opening 40, and the proximal portion 53R is configured to wrap circumferentially around the proximal portion 39P of the body 39. The proximal portion 53R of the flex circuit includes the coil traces X and Y, and one or more elongated connection pads 79 that traverse over the coil traces X and Y and are generally perpendicular to the tail 53T when the proximal portion 53R is wrapped circumferentially around the proximal portion 39 of the body.

In some embodiments, one or more ring electrodes 21 are carried on the housing 13, as shown in FIG. 4. In the illustrated embodiment, a first ring electrode 21A having a predetermined width W1 is slipped over the distal end of the housing 13 and moved proximally onto the proximal portion 39P until the ring electrode abuts tightly with the annular ridge 43 acting as a stop. A first spacer 60A having a predetermined width W2 is then slipped over the distal end of the housing 13 and moved proximally until it abuts tightly with the first ring electrode 21A. A second ring electrode 21B having a predetermined with W3 is slipped over the distal end of the housing 13 and moved proximally until it abuts tightly with the first spacer 60A. A second spacer 60B having a predetermined width W4 is slipped over the distal end of the housing 13 and moved proximally until it abuts tightly with the second ring electrode 21B. Accordingly, the ring electrodes 21A, 21B can be advantageously arranged with tight tolerances for improved mapping and/or ablation performance. The lead wires 30R for the ring electrodes 21A, 21B pass through respective through-holes 56 and 57 (see FIG. 5A) formed in the sidewall of the housing proximal portion 39P for connection to the respective ring electrodes.

In some embodiments, the ring electrodes are electrically connected to the underlying elongated circumferential connection pads 79 provided on the proximal portion 53R of the flex circuit 53 (see FIG. 9) that is wrapped around the proximal portion 39P of the body 39 below the ring electrodes and the spacers.

It is understood that the housing 13 may be configured with any desired longitudinal length for accommodating a corresponding plurality of ring electrodes, whose predetermined width and spacing between adjacent ring electrodes on the outer surface of the housing 13 may be varied as desired.

In some embodiments, the distal section 15 includes a force sensor 61 having a distal on-axis stem 63 with a lumen, an annular proximal portion or ring 62 perpendicular to the stem 63, and a plurality (e.g., three, although only two are shown in FIG. 4) radial strain gauges 72 extending between the stem 63 and the annular ring 62. The ring 62 is configured to fit onto the neck 44 of the housing 13. In that regard, a proximal end of the neck 44 may have a plurality of fasteners or snaps 64 that engage with the distal edge of the ring 62 to secure the force sensor onto the housing 13. Each strain gauge 72 has respective electrical leads 65 and connection pads 66 that allow electrical signals arising from the strain gauges to pass onto the flex circuit 53 and pass proximally along the catheter through the deflection section 14 and the catheter body 12 via the cables 58.

Mounted on an extended distal end 63D of the stem 63 is the distal tip electrode 17, as shown in FIG. 4. The distal tip electrode 17 includes a shell portion 71 and a proximal plug portion 73 (shown in broken lines) which seals an open proximal end of the shell portion to create an interior chamber 70. A distal end of the lead wire 23T (see FIG. 2 and FIG. 3, not shown in FIG. 4) is potted in a blind hole (not shown) in the plug portion 73 and the lead wire 23T extends through the lumen of the stem 63 of the force sensor 61. The irrigation tubing 24 (see FIG. 2 and FIG. 3, not shown in FIG. 4) also extends through the lumen with its distal end extending into the interior chamber 70 defined by the shell portion 71 of the tip electrode 17. A plurality of irrigation ports 74 are formed in the shell portion 71 so that fluid delivered by the irrigation tubing 24 into the interior chamber 70 can exit the distal tip electrode 17 via the irrigation ports 74. The plug portion 73 has an axial through-opening that receives the extended distal end 63D of the force sensor 61 and secures the force sensor 61 relative to the shell portion 71 so that any force exerted on the shell portion 71, for example, when the shell portion 71 contacts tissue surface, is imparted to the plug portion 73 and the stem 63 of the force sensor 61 in activating the strain gauges 72 to transmit electrical signals to the connection pads 66 of the flex circuit 53, as shown in FIG. 8. The extended distal end 63D has a smaller outer diameter relative to the stem 63 so as to create a stop 63 that abuts a proximal face of the plug portion 73 and prevents plug portion 73 from moving proximally and interfering with the action of the stem 63 in responding to a force that is applied to the distal tip electrode. Traces 75 transmit the strain electrical signals to the cables 58 (see FIG. 2 and FIG. 3, not shown in FIG. 4) via connection pads 78.

In some embodiments, a short nonconductive tubing 95 (see FIG. 4) extends between the tip electrode 17 and the second spacer 60B, circumferentially surrounding, protecting and providing a fluid-tight seal around the force sensor 61. The tubing 95 is sufficiently flexible so as not to interfere with deformation of the strain gauges 72 of the force sensor 61 when sensing contact and force of the tip electrode 17 against tissue.

Having a micro-injection-molded body, the housing 13 performs as a single, unitary body and component providing a multitude of functions, including an distal anchor for the puller tensile member and a support for various components, including, the flex circuit, the force sensor, the x/y/z-axes coils, the ring electrodes and their spacers. The lumen 41 of the housing 13 can house additional components, as needed or desired. The housing 13 provides cost savings in terms of supply and manufacturing costs. Micro injection molding can allow more intricate and detailed 3-D geometry in the housing 13.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Notably, the drawings are not necessarily to scale, and any one or more features of any one or more embodiments may be included in any other one or more embodiments in addition to or in lieu of any feature, as desired or appropriate. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrophysiology catheter having:
    an elongated catheter body;
    a deflection section distal of the catheter body;
    a distal electrode section having:
        a housing with a generally-cylindrical, hollow housing body with an outer surface with a circumferential recess, the housing body defining a lumen and an opening in a sidewall allowing access into the lumen,
        a magnetic field sensing coil wire situated in the circumferential recess, and
        a flex circuit having a first portion supported on the outer surface of the housing body and a second portion extending into the lumen via the opening in the housing body, wherein the flex circuit has a first magnetic field sensing coil trace, and a second magnetic field sensing coil trace generally perpendicular to the first magnetic field sensing coil trace,
    a control handle proximal of the catheter body.

2. The catheter of claim 1, wherein the housing body has a micro-injection molded construction.

3. The catheter of claim 1, wherein the first and second magnetic field sensing coil traces are electrically connected to one or more cables extending through the catheter body and the deflection section.

4. The catheter of claim 3, wherein the magnetic field sensing coil wire is generally perpendicular to the first and second magnetic field sensing coil traces.

5. The catheter of claim 1, wherein the distal electrode section includes a ring electrode and a ring spacer on the outer surface of the housing body.

6. The catheter of claim 5, wherein the housing body has a ridge at its proximal end, and the ring electrode abuts the ridge, and the ring spacer abuts the ring electrode.

7. The catheter of claim 5, wherein the housing body has a ridge at its proximal end, and the ring spacer abuts the ridge, and the ring electrode abuts the ring spacer.

8. The catheter of claim 1, wherein the distal electrode section further comprises a force sensor mounted on a distal end of the housing body.

9. The catheter of claim 8, wherein the force sensor has a plurality of strain gauges electrically connected to the flex circuit.

10. An electrophysiology catheter having:
   an elongated catheter body;
   a deflection section distal of the catheter body;
   a distal electrode section having:
     a housing with a generally-cylindrical, hollow housing body with an outer surface, the housing body defining a lumen and an opening in a sidewall allowing access into the lumen,
     a flex circuit having a first portion supported on the outer surface of the housing body and a second portion extending into the lumen via the opening in the housing body, and
     a force sensor mounted on a distal end of the housing body, the force sensor having a plurality of strain gauges electrically connected to the flex circuit, and the force sensor having an on-axis stem and an annular ring generally perpendicular to the stem, the strain gauges extending between the stem and the annular ring; and
   a control handle proximal of the catheter body.

11. The catheter of claim 1, wherein the distal electrode section includes a tip electrode distal of the housing body, the tip electrode having a shell portion, a plug portion and an internal chamber configured to receive fluid.

12. The catheter of claim 11, wherein the catheter includes a fluid tubing extending through the catheter body and the deflection section and into the distal electrode section, the fluid tubing having a distal end configured to pass fluid into the internal chamber of the tip electrode.

13. The catheter of claim 1, further comprising a puller tensile member having a U-bend portion anchored in the housing body.

14. The catheter of claim 13, wherein the housing body has a through-opening through which the puller tensile member extends.

15. The catheter of claim 13, wherein the housing body has two through-openings through which the puller tensile member extends.

16. The catheter of claim 13, wherein the housing body has a recess in which the U-bend portion of the puller tensile member lies.

17. The catheter of claim 16, wherein the recess on the housing body is arcuate around a distal opening of the lumen.

18. The catheter of claim 1, wherein the housing body has a step between a distal portion with a smaller outer diameter and a proximal portion with a larger diameter, the first portion of the flex circuit being supported on the distal portion of the housing body.

19. The catheter of claim 18, wherein a magnetic sensing coil wire is wound on the proximal portion of the housing body.

* * * * *